US00PP14904P2

(12) United States Plant Patent
Fear et al.

(10) Patent No.: US PP14,904 P2
(45) Date of Patent: Jun. 15, 2004

(54) RASPBERRY PLANT NAMED 'DRISCOLL DULCITA'

(50) Latin Name: *Rubus idaeus L.*
Varietal Denomination: Dulcita

(75) Inventors: Carlos D. Fear, Aptos, CA (US); Richard E. Harrison, Aptos, CA (US); Fred M. Cook, Aptos, CA (US); Gavin Sills, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 37 days.

(21) Appl. No.: 10/306,459

(22) Filed: Nov. 27, 2002

(51) Int. Cl.[7] ..... A01H 5/00
(52) U.S. Cl. ..... Plt./204
(58) Field of Search ..... Plt./204

*Primary Examiner*—Bruce R. Campell
*Assistant Examiner*—Susan B. McCormick
(74) *Attorney, Agent, or Firm*—Pennie & Edmonds LLP

(57) ABSTRACT

The present invention relates to a new and distinct cultivar of raspberry plant named Dulcita. The new cultivar is distinguished from other raspberry cultivars by its fruit firmness, fruit structure, good flavor and yield. The new cultivar is distinguished from its seed parent by having larger fruit with better flavor. The new cultivar is distinguished from its pollen parent by producing a higher yield of fruit.

3 Drawing Sheets

1. BACKGROUND OF THE INVENTION

The new cultivar of raspberry plant was developed from the hybridization of the selection 'Gloria' (U.S. Plant Pat. No. 11,067) as the seed parent with the selection 'N257.1' (an unpatented variety) as the pollen parent. The parents were crossed in 1994, whereafter fruit and seed were collected to produce seedlings for field planting in Watsonville, Calif. in 1994. The new cultivar was selected from these seedlings in 1995 for its excellent fruit firmness, fruit structure, and flavor. The new cultivar has been asexually propagated by in vitro shoot tip culture, root sucker division and root cuttings at the Cassin Ranch in Santa Cruz county, Calif. and has been shown to maintain the desired and distinguishing characteristics after propagation over several generations.

2. SUMMARY OF THE INVENTION

The present invention provides a new and distinct cultivar of red raspberry plant named 'Dulcita'. The cultivar is botanically identified as *Rubus idaeus* L. The 'Dulcita' red raspberry plant produces a primocane crop which begins in mid to late July and continues until mid-October. The floricane crop begins in late May and continues until late July. Both the primocane and floricane yields are high relative to other comparable varieties. The fruit of 'Dulcita' is notably quite firm and very consistent with regard to its size and shape throughout its harvest period. The flavor is sweet and the fruit of 'Dulcita' separates easily from its receptacle.

3. BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics.

4. DETAILED BOTANICAL DESCRIPTION

Figure 1:
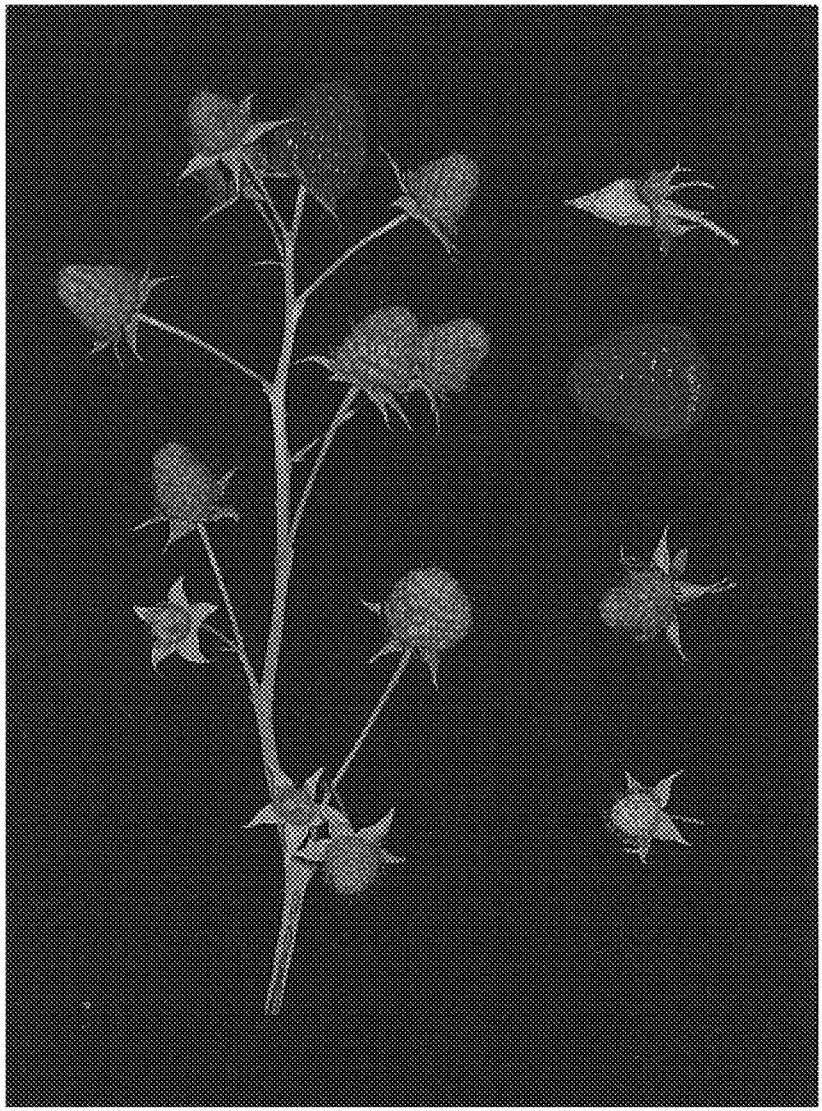
FIG. 1 is a photograph of 'Dulcita' primocane fruit in various stages of development.
Figure 2:
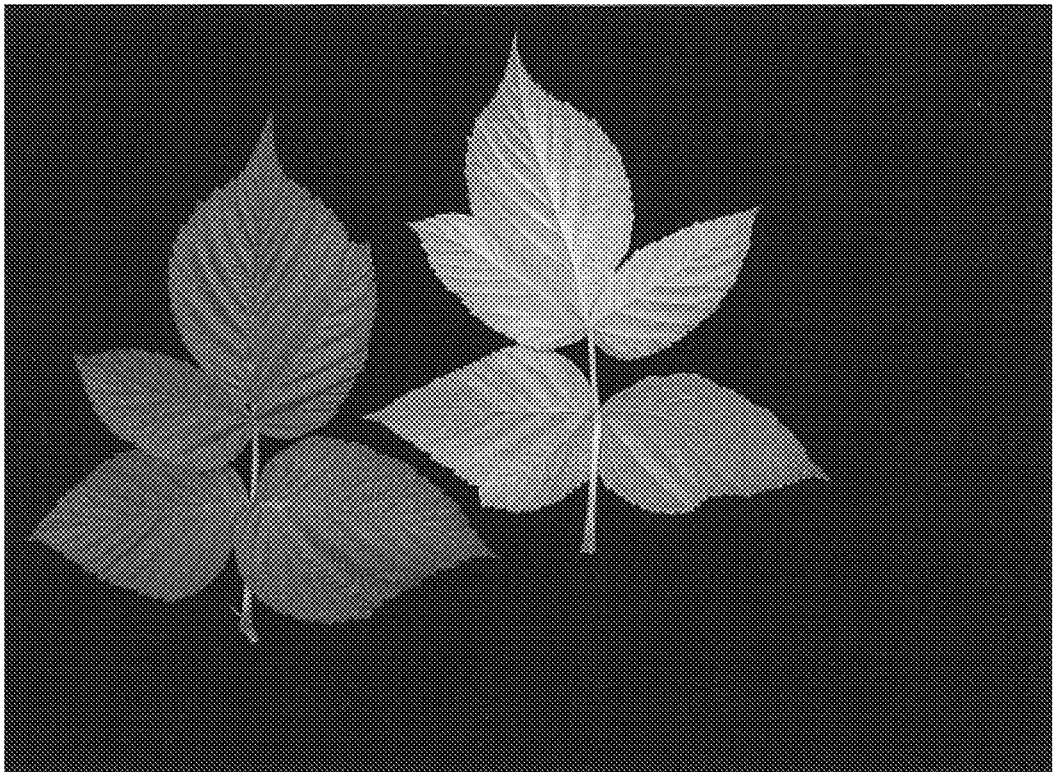
FIG. 2 is a photograph of 'Dulcita' primocane leaves showing upper and lower surfaces.
Figure 3:
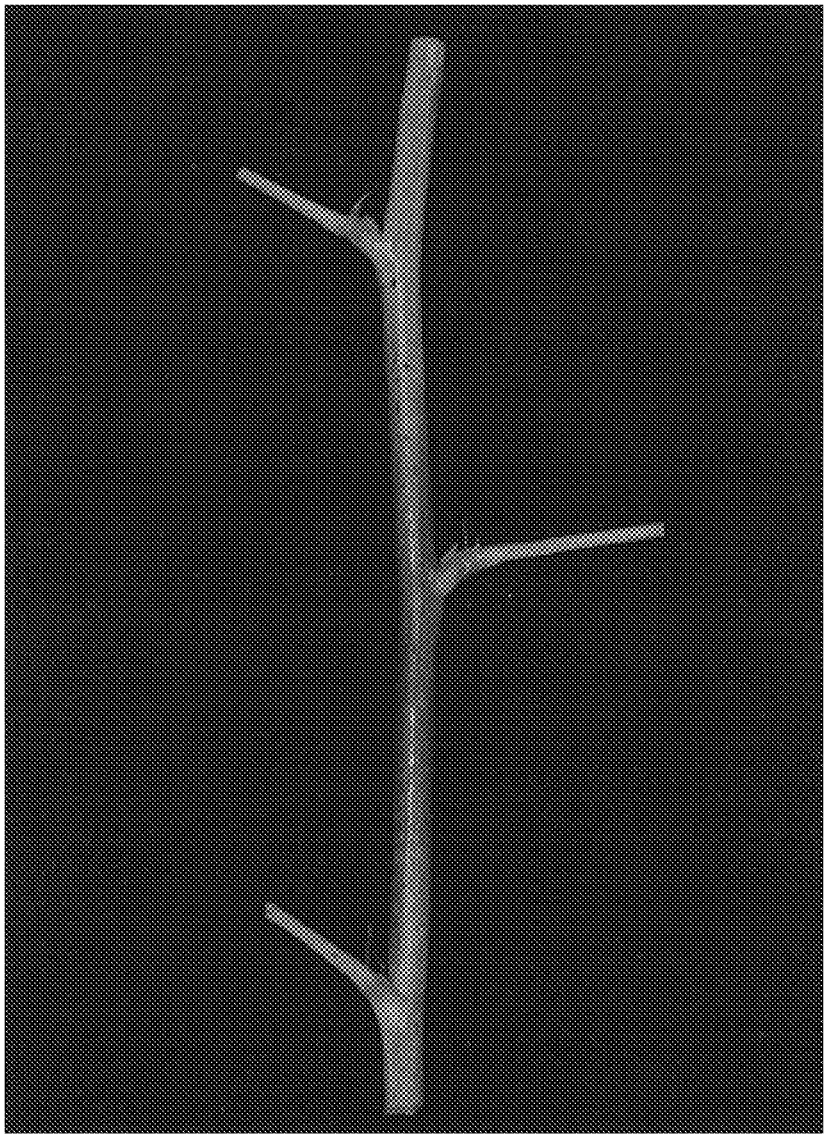
FIG. 3 is a photograph of 'Dulcita' primocane shoot.

The following detailed description of the new raspberry cultivar, 'Dulcita' is based upon observations taken of plants and fruit grown in Watsonville, Calif. between 2001 and 2002, and is believed to apply to plants of the 'Dulcita' cultivar grown in similar conditions of soil and climate elsewhere.

Throughout this specification, color names beginning with a small letter signify that the name of the color, as used in common speech, is aptly descriptive. Color data followed by an alphanumeric code designates the color according to The R.H.S. Colour Chart published by The Royal Horticultural Society of London, England. Color designations, color descriptions, and other phenotypical descriptions may deviate from the stated values and descriptions depending upon variation in environmental, seasonal, climatic and cultural conditions.

Table 1 provides information on the plant and fruit characteristics of the new cultivar 'Dulcita' compared with characteristics of the unpatented raspberry cultivar 'Heritage'. Observations of the cultivars were taken under similar conditions.

The new variety is particularly characterized and distinguished from other cultivars by its fruit firmness, fruit structure, good flavor and yield.

The fruit color of 'Dulcita' is a medium red at harvest but darkens after harvest to a deeper color. Fruit of 'Dulcita' separates easily from the receptacle and is of excellent firmness at harvest. The fruit of 'Dulcita' is very consistent in size and shape throughout the harvest period with good flavor.

The floricane yields of 'Dulcita' are high relative to the variety 'Heritage'. 'Dulcita' is distinguishable from its pollen parent, selection 'N257.1', by producing a higher yield of fruit. The new cultivar is distinguished from its seed parent, selection 'Gloria', by having larger fruit with better flavor.

4.1 DISEASE AND STRESS RESISTANCE

Resistance is unknown to powdery mildew. Cold tolerance of the new cultivar has not been established. Post harvest fruit rot resistance is good in comparison over many selections and varieties.

TABLE I

PLANT CHARACTERISTICS OF 'DULCITA'

| | Dulcita | Heritage |
|---|---|---|
| General | | |
| Plant size | Medium | Large |
| Growth habit | Erect | Erect |
| Productivity | Medium | Medium |
| Self-fruitfulness | Self-fruitful | Self-fruitful |
| Time of bud burst | Late | Late |
| Primocane fruiting | | |
| Percent of cane length flowering as primocane | 30–50 | 20–40 |
| Percent of total yield | 48 | 53 |
| Primocanes | | |
| Number of young shoots | Medium | Medium |
| Number fruiting laterals/cane | 17 | 18 |
| Young shoot pigmentation | Medium | Medium |
| Length (cm) | 203 | 196 |
| Time of shoot emergence | Medium | Very late |
| Glaucosity (waxy bloom) | Weak | Weak |
| Strength | Medium | Medium |
| Cane cross section (from mid cane of primocane) | Rounded to angular | Rounded |
| Dormant cane color | brown to tan | brown to purple brown |
| Prickles | | |
| Pigmentation | brown to purple | green-brownish to green |
| Density on young shoots | Medium | Dense |
| Attitude of tip | Downward | Downward |
| Size: Length (base to tip) at 1 m height at the end of season (mm) | 1 | 1 |
| Texture | Heavy | Rigid |
| Presence and distribution on petioles | Present, irregularly distributed | Present, irregularly distributed |
| Pubescence on canes | Absent | Absent |
| Internodal distance (cm) (at central 1/3 of cane) | 6.7 | 5.3 |
| LEAVES | | |
| Color | | |
| Face | 147A | 147A |
| Underside | 148C | 148B |
| Relief between veins | Strong | Very weak |
| Cross section | Flat (Plane) | Concave |
| Glossiness | Medium | Medium |
| Petiole | | |
| Length (cm) | 6.4 | 7.7 |
| Pigmentation of Upper Surface | Very light-red purple | Lightly |
| Pigmentation of underside | yellow-green | Unpigmented |
| Petiolule length | Short | Very short |
| Stipule orientation | Erect | Erect |

TABLE I-continued

PLANT CHARACTERISTICS OF 'DULCITA'

| | Dulcita | Heritage |
|---|---|---|
| Arrangement | Compound | Compound |
| Number of leaflets | Usually 5 | Sometimes 3 sometimes 5 |
| Overlapping of lateral leaflets | Overlapping | Free to touching |
| Terminal leaflet | | |
| Length(cm) | 12.5 | 14.6 |
| Width (cm) | 8.6 | 7.8 |
| Shape | Ovate | Ovate |
| Tip | Acuminate | Acuminate |
| Base | Cordate | Acute to rounded |
| Margin | Doubly serrate | Doubly serrate |
| Lateral leaflets (basal pair) | | |
| Length (cm) | 9.9 | 14.7 |
| Width (cm) | 7.6 | 8.6 |
| Rachis length between terminal leaflet and adjacent lateral leaflets (cm) | 4.1 | 1.5 |
| Overlap | Yes | Free |
| Orientation | Opposite | Opposite |
| Shape | Ovate | Ovate |
| Tip | Acuminate | Acuminate |
| Base | Oblique | Oblique |
| Margin | Doubly serrate | Doubly serrate |
| FLOWERS | | |
| Flowering period | | |
| Primocane | 14 weeks, Mid June to mid September | 19 weeks, Late May to late September |
| Floricane | 10 weeks, Early April to mid June | 10 weeks, Late March to mid June |
| Flower diameter (cm) | 1.5 | 1.8 |
| Petal | | |
| Length (cm) | 0.9 | 0.8 |
| Width (cm) | 0.4 | 0.3 |
| Pedicel coloration | Absent | Present, strong intensity |
| FRUIT | | |
| Harvest season | | |
| Primocane | Late July-mid October | Early July-early November |
| Floricane | Late May-late July | Late May-late July |
| Fruiting laterals (floricane) | | |
| Length (4th lateral from tip) (cm) | 67.8 | 49.8 |
| Number of fruit per lateral | 19 | 20.3 |
| Color | Medium red | Medium red |
| Immature | 45C | 42C |
| Maturing | 46A | 46A |
| Mature Fruit | 46A | 59A |
| Glossiness | Weak | Medium |
| Shape | Ovate | Ovate |
| Dimensions | | |
| Size | Medium | Small |
| Length(mm) | 21 | 17 |
| Width(mm) | 21 | 18 |
| Length: width ratio | 1.0 | 0.94 |
| Weight (g/Fruit) | | |
| Primocane | 3.9 | 3.1 |
| Floricane | 3.5 | 2.3 |
| Soluble solids (%) | 12.4 | 10.8 |
| Titratable acidity (% as citric acid) | 1.45 | 1.58 |
| Seed weight (mg) | 2.0 | 1.5 |
| Number druplets/fruit | 80 | 72 |

TABLE I-continued

| PLANT CHARACTERISTICS OF 'DULCITA' | | |
|---|---|---|
| | Dulcita | Heritage |
| Adherence to plug | Medium | Medium |
| Firmness | Medium firm | Firm |
| Yield | High | Medium |

4.2 NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531–5). Using a variety of oligonucleotide primers, alone or in combination, RAPD analysis of Dulcita and Heritage yielded DNA fragment patterns that uniquely distinguish each of these genetically distinct genotypes.

We claim:

1. A new and distinctive cultivar of raspberry plant, substantially as shown and described.

* * * * *